(12) United States Patent
Casas

(10) Patent No.: US 10,660,997 B2
(45) Date of Patent: May 26, 2020

(54) BLOOD PUMP WITH SENSORS ON HOUSING SURFACE

(71) Applicant: HeartWare, Inc., Miami Lakes, FL (US)

(72) Inventor: Fernando Casas, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 23 days.

(21) Appl. No.: 15/711,532

(22) Filed: Sep. 21, 2017

(65) Prior Publication Data
US 2018/0085505 A1 Mar. 29, 2018

Related U.S. Application Data

(60) Provisional application No. 62/398,931, filed on Sep. 23, 2016.

(51) Int. Cl.
*A61M 1/10* (2006.01)
*A61M 1/12* (2006.01)

(52) U.S. Cl.
CPC .......... *A61M 1/1015* (2014.02); *A61M 1/101* (2013.01); *A61M 1/1036* (2014.02); *A61M 1/122* (2014.02); *A61M 2205/3313* (2013.01); *A61M 2205/3317* (2013.01); *A61M 2205/3334* (2013.01); *A61M 2205/3375* (2013.01); *A61M 2230/205* (2013.01)

(58) Field of Classification Search
None
See application file for complete search history.

(56) References Cited

U.S. PATENT DOCUMENTS

| | | | | |
|---|---|---|---|---|
| 4,779,614 A | * | 10/1988 | Moise | F04D 3/005 415/900 |
| 4,801,830 A | * | 1/1989 | Ogino | H02K 29/08 310/268 |
| 4,957,504 A | * | 9/1990 | Chardack | A61M 1/1031 415/912 |

(Continued)

OTHER PUBLICATIONS

International Search Report and Written Opinion dated Dec. 11, 2017, for corresponding International Application No. PCT/US2017/052707 International Filing Date: Sep. 21, 2017 consisting of 13-pages.

*Primary Examiner* — Carl H Layno
*Assistant Examiner* — Manolis Pahakis
(74) *Attorney, Agent, or Firm* — Christopher & Weisberg, P.A.

(57) ABSTRACT

A blood pump has an inner housing and an actuator at least partially surrounded by the inner housing which is configured to drive a flow of blood within the body. An electronic component associated with a surface of the housing includes one or more thin film active electronic devices which implement one or more transducers configured to generate a signal based on movement associated with operation of the blood pump. An electromagnetic stator at least partially surrounds the inner housing and is configured to be magnetically coupled with the actuator in an energized state of the electromagnetic stator, wherein the electromagnetic stator may overlie at least a portion of the electronic component.

10 Claims, 10 Drawing Sheets

(56) References Cited

U.S. PATENT DOCUMENTS

| | | | | |
|---|---|---|---|---|
| 5,079,467 A * | 1/1992 | Dorman | F04D 29/108 | 310/156.12 |
| 5,385,581 A * | 1/1995 | Bramm | F04D 13/06 | 417/356 |
| 5,924,975 A * | 7/1999 | Goldowsky | F04B 17/046 | 600/16 |
| 6,053,705 A | 4/2000 | Schob et al. | | |
| 6,100,618 A | 8/2000 | Schoeb et al. | | |
| 6,116,862 A | 9/2000 | Rau et al. | | |
| 6,176,848 B1 | 1/2001 | Rau et al. | | |
| 6,264,635 B1 * | 7/2001 | Wampler | F04D 29/041 | 417/423.1 |
| 6,351,048 B1 | 2/2002 | Schob et al. | | |
| 6,640,617 B2 * | 11/2003 | Schob | A61M 1/101 | 73/54.01 |
| 6,817,836 B2 * | 11/2004 | Nose | F04B 49/06 | 415/900 |
| 6,949,066 B2 * | 9/2005 | Bearnson | A61M 1/101 | 600/16 |
| 7,070,398 B2 * | 7/2006 | Olsen | F16C 32/0448 | 417/353 |
| 7,112,903 B1 * | 9/2006 | Schob | F16C 32/0465 | 310/90.5 |
| 7,160,242 B2 * | 1/2007 | Yanai | F04D 15/02 | 600/16 |
| 7,284,956 B2 * | 10/2007 | Nose | F04B 49/06 | 128/898 |
| 7,997,854 B2 | 8/2011 | LaRose et al. | | |
| 8,007,254 B2 | 8/2011 | LaRose et al. | | |
| 8,897,873 B2 | 11/2014 | Schima et al. | | |
| 8,961,390 B2 | 2/2015 | LaRose et al. | | |
| 9,159,635 B2 | 10/2015 | Elolampi et al. | | |
| 9,281,415 B2 | 3/2016 | Bao et al. | | |
| 10,166,318 B2 * | 1/2019 | Yu | A61M 1/086 | |
| 2006/0229488 A1 * | 10/2006 | Ayre | A61B 5/02158 | 600/17 |
| 2010/0036487 A1 | 2/2010 | Crosby et al. | | |
| 2011/0200460 A1 * | 8/2011 | Nonaka | F04D 19/042 | 417/63 |
| 2011/0237863 A1 * | 9/2011 | Ricci | A61M 1/101 | 600/16 |
| 2011/0243759 A1 * | 10/2011 | Ozaki | A61M 1/101 | 417/279 |
| 2011/0293450 A1 * | 12/2011 | Grimes | F04B 17/03 | 417/420 |
| 2011/0313318 A1 * | 12/2011 | Rule | A61B 5/14532 | 600/581 |
| 2012/0211093 A1 * | 8/2012 | Grimes | F04B 17/03 | 137/334 |
| 2012/0245680 A1 * | 9/2012 | Masuzawa | A61M 1/1086 | 623/3.11 |
| 2012/0245681 A1 * | 9/2012 | Casas | A61M 1/1086 | 623/3.28 |
| 2012/0310036 A1 * | 12/2012 | Peters | A61M 1/101 | 600/16 |
| 2013/0204202 A1 * | 8/2013 | Trombly | A61M 5/172 | 604/207 |
| 2014/0062239 A1 | 3/2014 | Schoeb | | |
| 2014/0100413 A1 * | 4/2014 | Casas | A61M 1/1086 | 600/16 |
| 2014/0100414 A1 * | 4/2014 | Tamez | A61M 1/10 | 600/16 |
| 2014/0161651 A1 * | 6/2014 | Grimes | F04B 17/042 | 417/420 |
| 2014/0275723 A1 * | 9/2014 | Fritz, IV | A61M 1/1015 | 600/16 |
| 2016/0193396 A1 | 7/2016 | Taskin et al. | | |
| 2016/0302729 A1 * | 10/2016 | Starr | A61B 5/0004 | |
| 2016/0369790 A1 * | 12/2016 | Yavorsky | F04B 51/00 | |
| 2018/0169313 A1 * | 6/2018 | Schwammenthal | A61M 1/1024 | |
| 2019/0060543 A1 * | 2/2019 | Khanal | A61M 1/1086 | |

\* cited by examiner

BLOOD PUMP WITH SENSORS ON HOUSING SURFACE

CROSS-REFERENCE TO RELATED APPLICATION

This application is related to and claims priority to U.S. Provisional Patent Application Ser. No. 62/398,931, filed Sep. 23, 2016, entitled BLOOD PUMP WITH SENSORS ON HOUSING SURFACE, the entirety of which is incorporated herein by reference.

STATEMENT REGARDING FEDERALLY SPONSORED RESEARCH OR DEVELOPMENT n/a

TECHNICAL FIELD

The present disclosure relates to blood pumps and associated monitoring devices and methods.

BACKGROUND

Blood pumps can be inserted into or implanted within the body for a variety of medical purposes. For example, when the output of the heart is insufficient to meet the circulatory needs of a person or animal, a pump can be implanted to boost circulation. In a particular application, a pump can augment the blood flow from the left ventricle of the heart to the body in persons having diminished heart function, such pumps being referred to as left ventricular assist devices ("LVADs").

SUMMARY

The present invention advantageously provides for an implantable blood pump including an inner housing sized to be implanted within a body of a patient. A rotor is at least partially surrounded by the inner housing and configured to drive a flow of blood within the body. An electronic component is associated with a surface of the inner housing, the electronic component including one or more thin film active electronic devices, the one or more electronic devices implementing one or more transducers configured to generate a signal based on movement associated with operation of the blood pump. A stator at least partially surrounds the inner housing, the stator is magnetically coupled with the rotor and overlying at least one of the one or more transducers.

In another aspect of this embodiment, the one or more transducers include at least one transducer configured to sense a change in a magnetic field associated with movement of the rotor.

In another aspect of this embodiment, the one or more transducers comprise at least first and second transducers spaced apart from one another in at least a first direction parallel to a downstream direction of the blood flow.

In another aspect of this embodiment, the first transducer is configured to emit sonic energy and the second transducer is configured to receive sonic energy, respectively, wherein the sonic energy received by the second transducer is processable relative to the sonic energy emitted by the first transducer to determine a rate of blood flow through the pump.

In another aspect of this embodiment, the one or more transducers comprise a first transducer configured to emit infrared energy and a second transducer configured to receive infrared energy, respectively, wherein the infrared energy received by the second transducer is processable relative to the infrared energy emitted by the first transducer to determine an operating speed of the pump.

In another aspect of this embodiment, the one or more electronic devices are fabricated on an electrically insulating region at the surface of the housing.

In another aspect of this embodiment, the one or more transducers comprise an emitter of infrared energy and a detector of infrared energy, wherein the emitter and the detector of infrared energy are arranged across a lumen of the blood pump configured to carry blood in an operating state of the blood pump, and the detector is configured to receive infrared energy which passes through the blood in the lumen.

In another aspect of this embodiment, the one or more transducers includes a first plurality of transducers, wherein the electronic component further comprises a second plurality of transducers including a generator of infrared energy and a detector of infrared energy, wherein the detector is configured to receive infrared energy from the generator which passes through blood within the pump.

In another aspect of this embodiment, the second plurality of transducers are configured to generate a second signal from infrared energy received after passing through blood within the pump, the second signal representative of a level of oxygen saturation within the blood.

In another aspect of this embodiment, the one or more transducers includes a generator of ultrasonic energy and a detector of ultrasonic energy, wherein the generator and the detector are arranged across a lumen of the blood pump through which blood flows in an operating state of the blood pump, and the detector is configured to receive ultrasonic energy which passes through the blood from the generator.

In another aspect of this embodiment, the one or more transducers include at least one accelerometer, and the at least one accelerometer is configured to monitor vibration associated with operation of the blood pump.

In another aspect of this embodiment, the one or more transducers are configured to directly receive electromagnetic waves or mechanical energy within the body representative of a monitored bodily function and are configured to generate an electrical signal representative of the monitored bodily function.

In another embodiment, an implantable circulatory system includes a blood pump having a stator, a rotor configured to be electromagnetically rotated by the stator within the blood pump, and an electronic component associated with a surface of an inner housing of the blood pump, the electronic component including one or more thin film active electronic devices, the one or more electronic devices implementing one or more transducers configured to generate a signal based on movement associated with operation of the blood pump, the stator at least partially surrounding the inner housing and overlying at least one of the one or more electronic devices. An implantable signal processor is included and configured to process the signal from the one or more transducers and generate a signal indicative of a rate of blood flow through the blood pump.

In another aspect of this embodiment, the one or more transducers is positioned within a sealed space of the blood pump which precludes contact between blood and the one or more transducers in an operational state of the blood pump.

In another aspect of this embodiment, the one or more transducers is configured to generate the signal based on at least one from the group consisting of a position of the rotor and a displacement of the rotor relative to a prior position of the rotor.

In another aspect of this embodiment, the one or more transducers includes a generator of ultrasonic energy and a detector of ultrasonic energy, wherein the generator and the detector are arranged across a lumen of the blood pump through which blood flows in an operating state of the blood pump, and the detector is configured to receive ultrasonic energy which passes through the blood from the generator.

In another aspect of this embodiment, the one or more transducers include at least one accelerometer, and the at least one accelerometer is configured to monitor vibration associated with operation of the blood pump.

In another aspect of this embodiment, the one or more transducers are configured to directly receive electromagnetic waves or mechanical energy within the body representative of a monitored bodily function and are configured to generate an electrical signal representative of the monitored bodily function.

In yet another embodiment, a blood pump is configured for at least one of insertion or implantation within a living body includes an inner housing defining a major longitudinal axis. An impeller is circumferentially surrounded by the inner housing and configured to impel blood along the major longitudinal axis. An electronic component is associated with an outwardly facing surface of the inner housing and including one or more thin film active electronic devices, the one or more electronic devices implementing one or more transducers configured to generate a signal based on at least one from the group consisting of movement, position, and displacement of the impeller. The one or more transducers are positioned within a sealed space of the blood pump which precludes contact between blood and the one or more transducers in an operational state of the blood pump.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
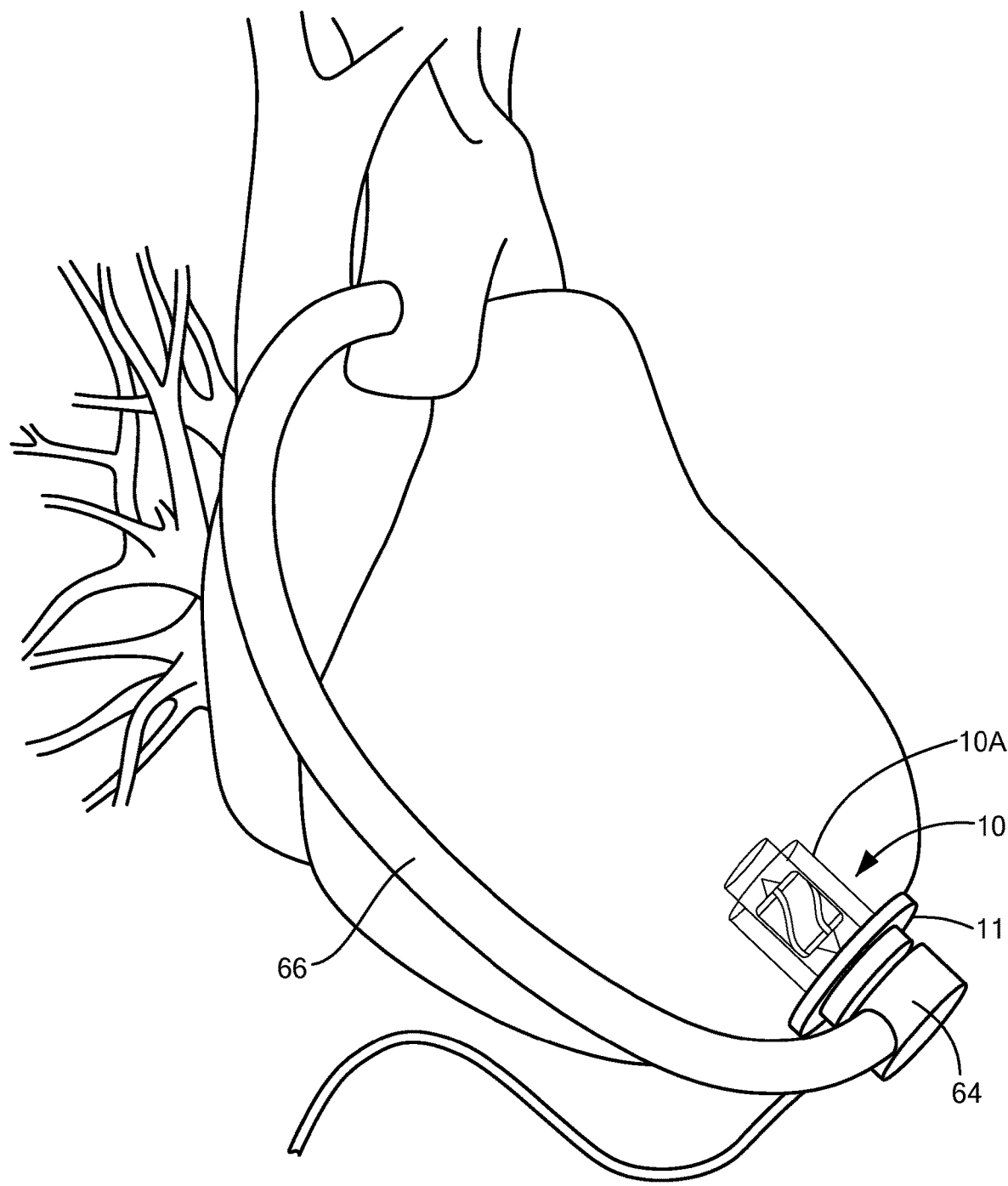
FIG. 1 is an illustration of a blood pump as may be implanted within the body to supplement the function of the heart in pumping blood to the body in accordance with an embodiment of the invention.
Figure 2:
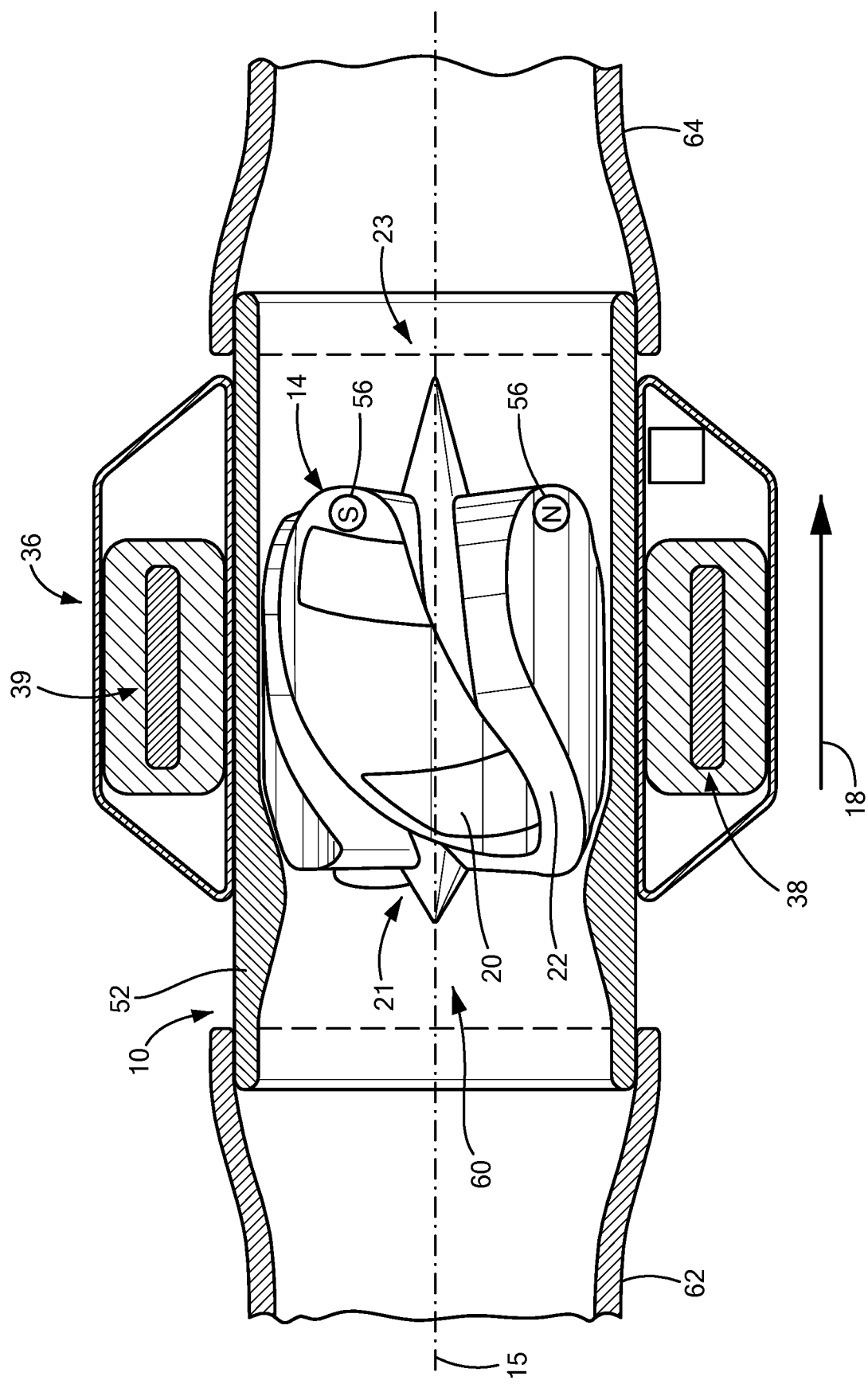
FIG. 2 is a detailed view of a blood pump which may be implanted or inserted in the body in accordance with an embodiment of the invention.

The operation of a blood pump inserted or implanted into the body can be monitored in several ways. However, greater options for monitoring operation of a blood pump would be desirable. Referring to FIGS. 1 and 2, a blood pump 10 implanted within the human body can be as seen in commonly owned U.S. Pat. No. 8,007,254 entitled "Axial Flow Pump with Multi-Grooved Rotor," the disclosure of which is incorporated by reference herein. The implanted blood pump 10 is coupled to a sewing ring 11 at an apex of the heart, with a portion 10A of the pump extending into the left ventricle of the heart. The portion 10A extending into the interior of the heart may have an impeller which is caused to rotate about a rotational axis to drive the blood downstream in an axial direction 18 within the pump. As further seen in FIG. 2, the impeller can be integral to a rotor 14 of an electric motor of the pump, the rotor caused to rotate about its rotational axis 15 by rotating magnetic poles generated by the coils of an electromagnetic stator 36 that surrounds the rotor in radial directions therefrom. Referring to FIGS. 1-2, downstream structure 64 coupled to the portion 10A of the pump within the heart may include a straight or curved chamber or a volute configured to direct pressurized blood into a cannula 66, which in turn is connected to the ascending aorta. In another example not shown in FIG. 1, the cannula 66 can instead be connected to the descending aorta.

Monitoring the operation of the pump and a rate of the blood flow therethrough can improve knowledge about the current condition of the pump, the effectiveness of the therapy to the patient, and the condition of the patient's circulatory system. Among various parameters, the rotational speed of the pump can be monitored.

One available way of determining a rotational speed of a rotating blood pump such as seen in FIGS. 1-2 is by measuring "back EMF." During operation, one or more of the coils of the blood pump are idle at any moment in time. The moving magnets of the rotor induce voltages in the idle coil, referred to as "back EMF". A sensor coupled to the circuitry powering the pump can be arranged to sample the back EMF in one or more of the coils during its idle state, and to supply the resulting sequence of samples to a processor, which can then examine the samples to detect a zero crossing or other recurring feature of the back EMF waveform, and determine the time between recurrences. This time is inversely proportional to the speed of rotation of the rotor. The processor can then repeatedly calculate the pump speed, for example, at a repetition rate many times the heart rate of the patient.

The blood flow rate through a blood pump can be determined based on a number of pump parameters which can include: the current in the coils; the speed of the rotor and the acceleration of the rotor of the pump, and the viscosity of the patient's blood. For example, as described in U.S. Pat. No. 8,897,873, the disclosure of which is incorporated by reference herein, the instantaneous flow through the pump can be estimated based on this information. The speed and acceleration may be taken from rotational speed data. The viscosity of the patient's blood normally may be input to the control system as a constant (e.g., based on the patient's hematocrit level), or may be estimated as, for example, by measuring the deceleration of the pump responsive to momentary interruption of power supply to the pump as described in U.S. Pat. No. 8,961,390, the disclosure of which is incorporated by reference herein. The current in the coils is proportional to the duty cycle of the pulse width modulated voltage applied to the coils by the pump interface. Such measurements may be repeated periodically as, for example, hourly or daily. Using such a model results in the estimate having a dynamic range of about 15 Hz.

In other examples, other parameters indicative of flow may be used, and/or different calculations may be employed, to estimate a flow rate of blood.

As further seen in FIG. 2, a rotor of an exemplary axial flow blood pump 10 can be partially magnetically suspended within a lumen 60 of the pump by an electromagnetic stator 36 surrounding the rotor 14 in radial directions, when the stator 36 is energized. An inner housing 52 that surrounds the lumen 60 can be constructed of non-ferromagnetic material, allowing magnetic fields produced by the stator 36 and the rotor to pass therethrough. In one embodiment, the inner housing can have a tubular shape. In particular examples, the inner housing 52 of the pump housing can be made of ceramic material, glass or polymer such as can be formed through a molding and/or machining process, or alternatively, alumina, titanium or other suitable metal. Thus, a rotating magnetic field produced by the stator 36, coupled with magnetic poles of the rotor, causes the rotor to rotate. In the example shown in FIG. 2, the electromagnetic stator 36 can be constructed of an iron core 38 on which windings shown generally at 39 are wrapped which, when energized, generates a rotating magnetic field which causes the rotor to rotate. The rotor functions as an impeller of the pump, having channels 22 functioning as fluid flow paths extending from a leading end 21 of the rotor to a trailing end 23 for impelling the blood in a substantially axial direction 18 parallel to a rotational axis 15 of the pump.

In some cases, the rotor 14 may be suspended by magnetic forces between magnetic poles on the rotor and corresponding magnetic poles or a magnetic field generated by the stator 36 during operation. In addition, the interaction of magnetic forces between the rotor and stator also help to maintain the axial position of the rotor within the inner housing 52, and to some extent, the radial position of the rotor as well. Typically, the rotor and electromagnetic stator 36 are disposed very close to one another, such that the magnetic field from each reaches the other with little diminution. Placing the rotor and stator close to one another can also assist in maintaining radial or axial stiffness of the pump during its operation.

Alternatively, or in addition thereto, the rotor may have hydrodynamic thrust bearing surfaces 20 thereon which are proximate an inner surface of the lumen 60 of the blood pump. In operation while the rotor spins within the pump, the hydrodynamic thrust bearing surfaces help maintain a radial position of the rotor within the lumen, and provide radial stability during operation.

FIG. 2 further shows the pump 10 as may be coupled with further structure, for example, upstream structure such as a pump inlet housing 62 positioned in the vicinity of or upstream from the leading end 21 of the rotor, and downstream structure 64 such as a volute, flow diverter, housing, or cannula in the vicinity of or downstream from the trailing end 23 of the rotor. The pump inlet housing 62 and the downstream structure 64 may be attached to the inner housing 52 or in some cases may be integral therewith.

Figure 3:
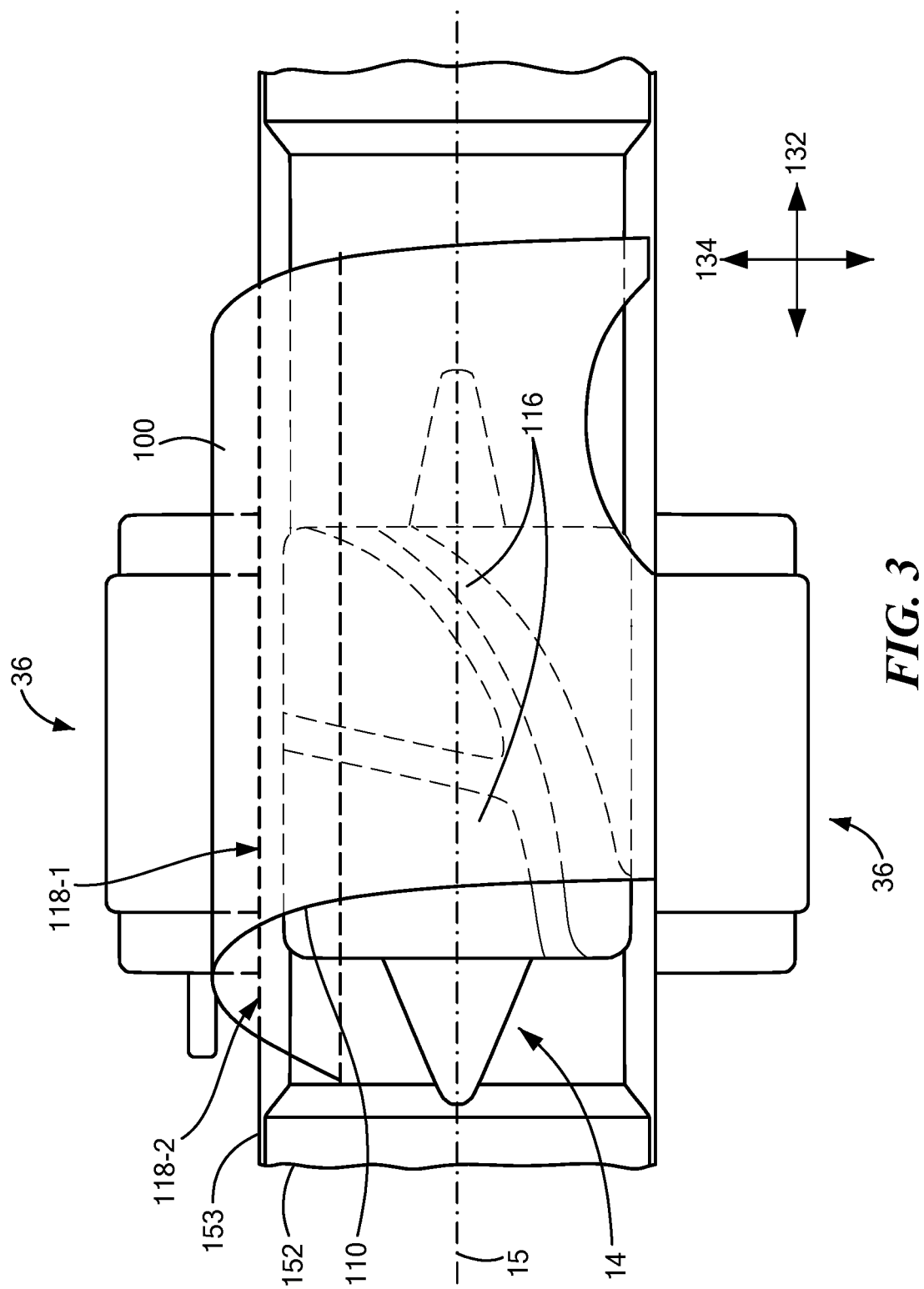
FIG. 3 illustrates a blood pump having an additional electronic component thereon configured to monitor operation of the blood pump in accordance with an embodiment of the invention.
Figure 4:
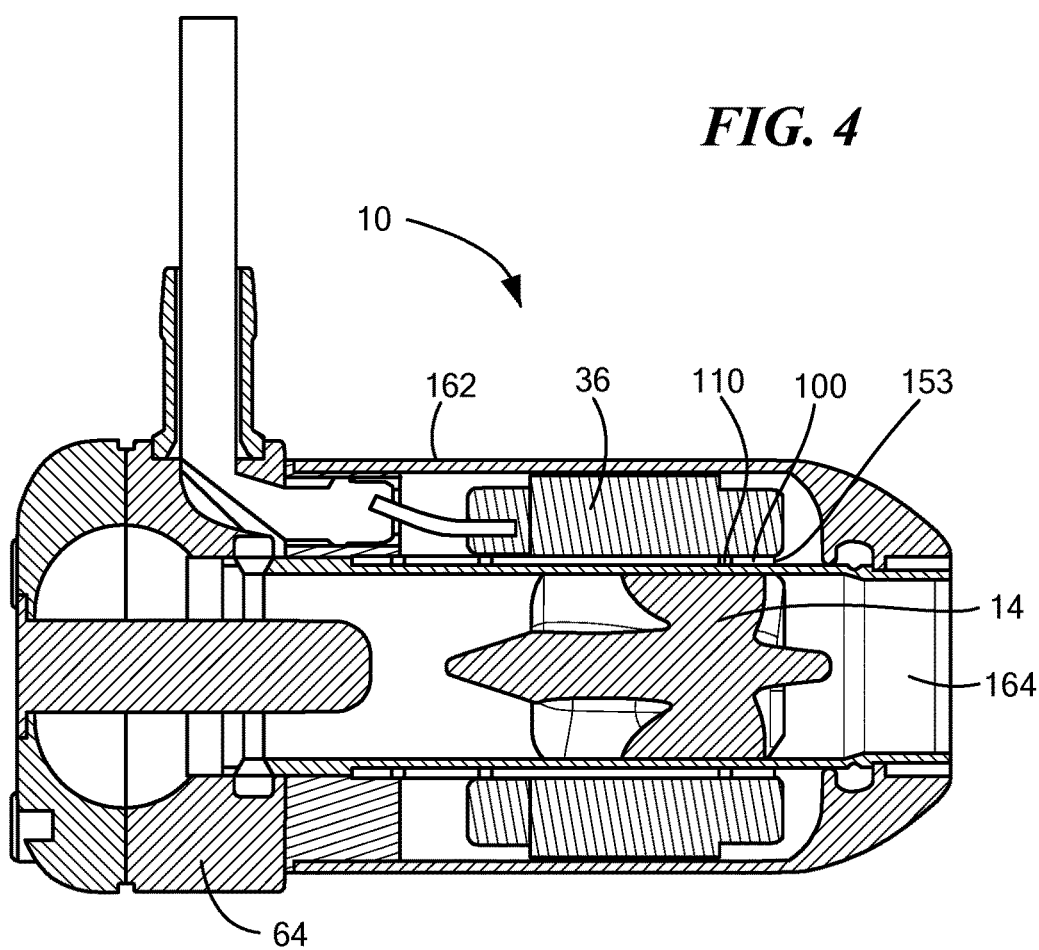
FIG. 4 is a sectional view further illustrating the blood pump shown in FIG. 3 in accordance with an embodiment of the invention.
Figure 5:
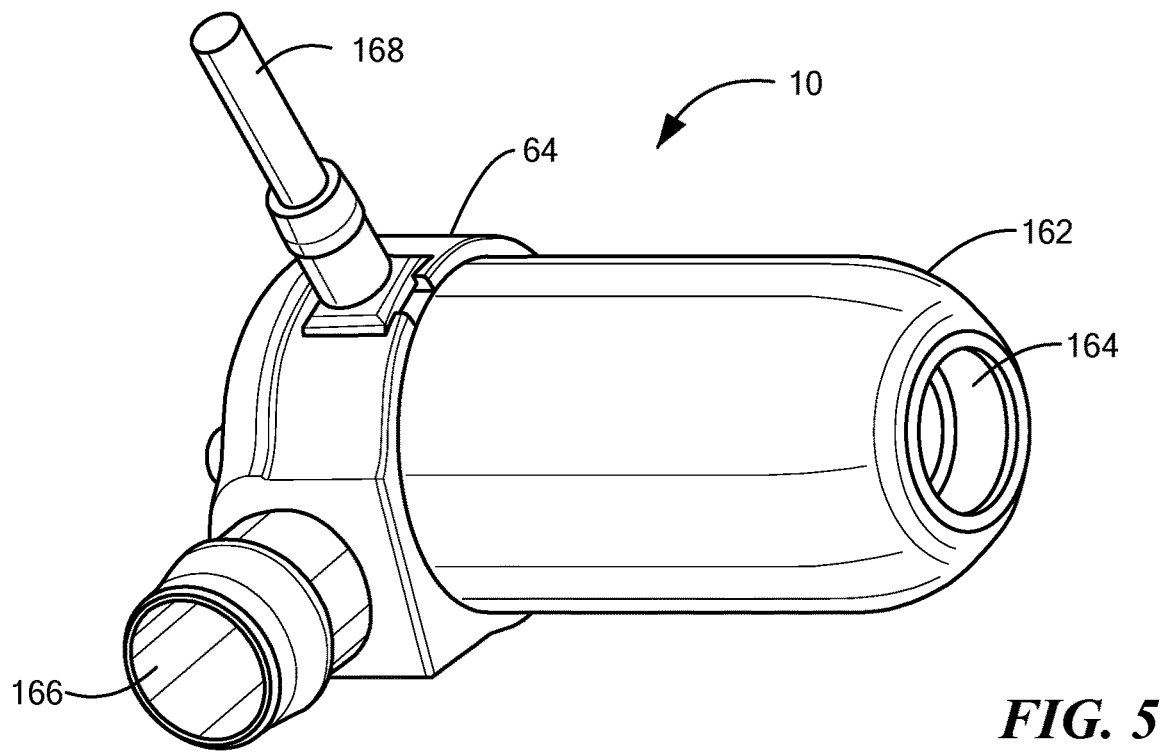
FIG. 5 is a perspective view further illustrating the blood pump shown in FIGS. 3 and 4 in accordance with an embodiment of the invention.
Figure 6:
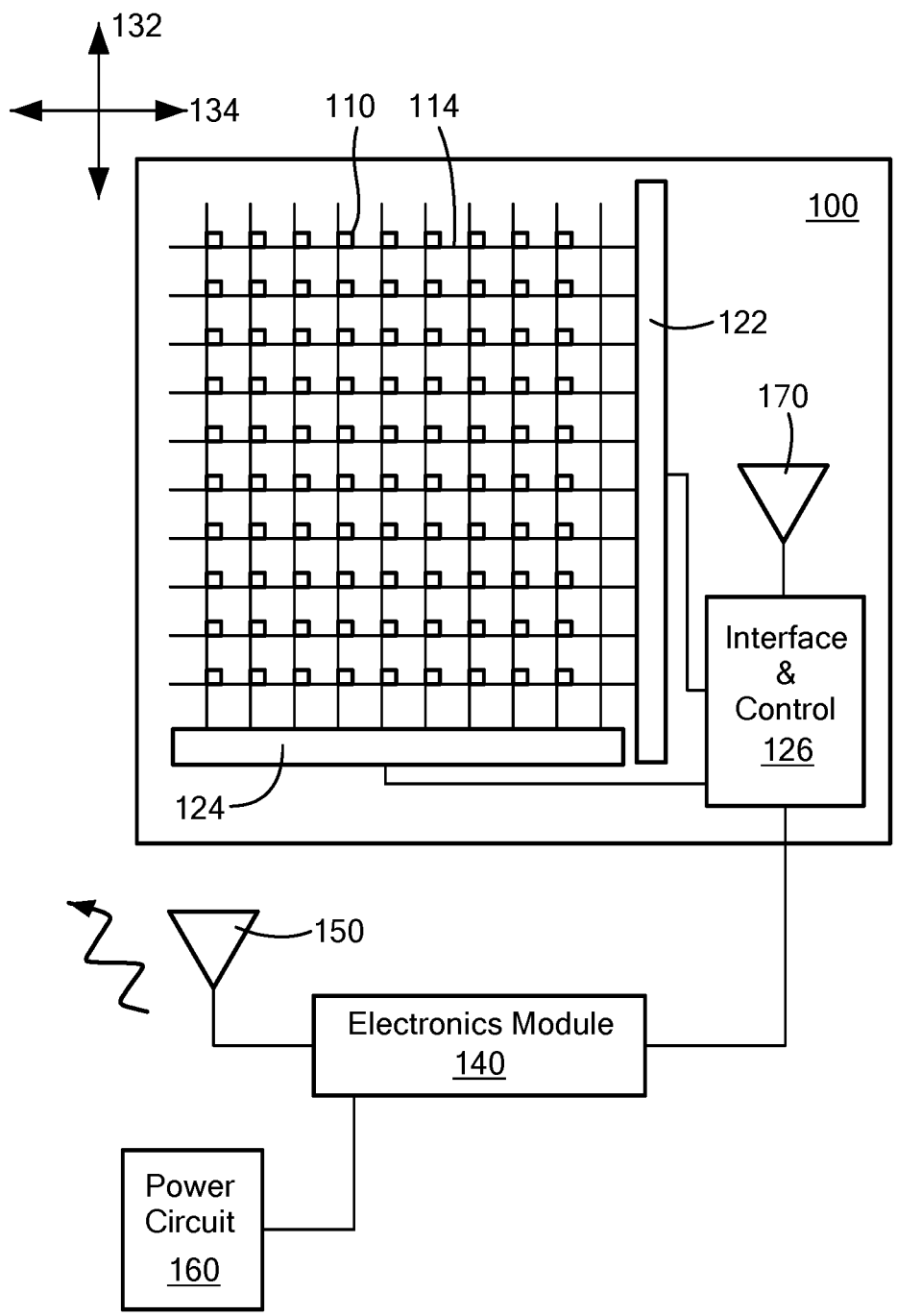
FIG. 6 is a schematic diagram further illustrating components of a blood pump monitoring system.

Referring now to FIGS. 3 through 6, a system is shown for monitoring an operating state of a blood pump suitable for implanting or inserting within the body of a person or animal. As depicted in FIGS. 3, 4 and 6, an electronic component 100 is shown associated with a surface 153 of an inner housing 152 that at least partially surrounds an actuator of the blood pump, such as a rotor 14 or impeller of the blood pump. The electronic component 100 can be configured to generate a signal based on movement of the actuator associated with operation of the blood pump.

FIGS. 4-5 further illustrate details of pump 10 which may include an outer housing 162 which overlies and encases the stator 36, electronic component 100, the surface 153 of the inner housing or other structure within a sealed space, and which construction precludes contact between the stator, the electronic component and the surface 153 of the inner housing with blood. Blood is driven through the pump from an inlet of the pump shown at 164 towards an outlet 166 of the downstream structure 64 as shown. A power cable 168 is further illustrated which includes a plurality of electrical conductors for supplying power and ground to the pump and which may include additional conductors which can be electrically coupled with the electronic component 100 for monitoring operation of the pump.

Figure 7:
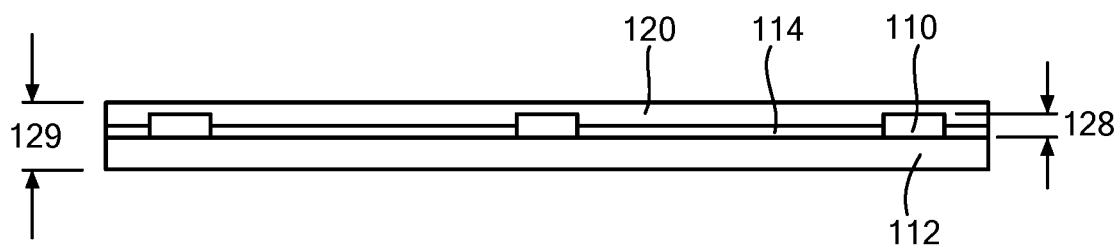
FIG. 7 depicts an electronic component in accordance with one embodiment of the invention.

The electronic component 100 contains one or more active electronic devices 110 which are thin and relatively flat. Referring to FIG. 7, a typical thickness 128 of each device 100 is 0.1 millimeter ("mm") or less. In one embodiment, each device 110 can be covered by a relatively thin encapsulation 120 (FIG. 7) having a thickness of 25 to 500 microns, for example. Typically, the entire thickness 129 of the electronic component is 1 mm or less. In particular examples, the entire thickness 129 can be 0.5 mm or less, 0.3 mm or less or 0.2 mm or less. The electronic component further includes a plurality of electrically conductive traces 114 which extend in directions between the electronic devices which can be configured to conduct power, ground and/or transmit signals to or from individual ones of the electronic devices. In one example, the electronic devices can be thin film active electronic devices. The electronic devices can be thin film transistors of traditional Group IV (silicon, germanium) or Group III-V compound semiconductor materials which can be fabricated to the required dimensions. In some cases, the electronic devices can be or include organic thin film transistors.

In a particular example, the electronic devices include or implement one or more transducers configured to generate a signal based on movement associated with an operating state of the blood pump. For example, one or more transducers can be arranged at one or more locations distributed over an area of the surface 153 of the inner housing and are configured to detect or sense movement of an actuator of the pump which is configured to drive a flow of blood. As further seen in FIGS. 3 and 4, because the electronic component 100 is thin and conforms to the surface 153 of the inner housing, the electromagnetic stator 36 may be disposed overlying some or all electronic devices of the electronic component. Thus, the one or more electronic devices, or in a particular example, the totality of the electronic component 100 can be disposed between the surface 153 of the inner housing and the electromagnetic stator 36.

As further seen in FIGS. 3 and 6, in one embodiment, the electronic devices 110 can be arranged in an M×N array of the electronic devices which are distributed at discrete locations in first and second transverse directions 132, 134 relative to the surface 153. At least one of M and N is greater than or equal to two. Typically, both M and N are greater than or equal to two.

The electronic devices can be distributed over an area spanning an arc about the rotational axis 15 of the rotor, and be coupled with other circuitry 122, 124 at edges, which may include amplifiers, state logic, switching and/or decoder circuitry, among others, which can be utilized for determining and amplifying signals received from individual devices 110 or groups of the devices 110. Interface and control circuitry 126 may also be included on the component, such circuitry configured to assist in handling commands from an electronics module 140 which may also be implanted within the body. In a further example, an antenna 170 can be coupled to the interface and control circuitry 126 which can be used to receive and/or transmit data and/or commands from and to circuitry external to the body. In one embodiment, circuitry 126 is coupled by a percutaneous driveline (not shown) extending through the skin of the patient to external circuitry which may include electronics module 140.

When the electronics module is implanted within the body, in some examples, the module can incorporate a transceiver configured to transmit and/or receive data and commands via antenna 150 to and from a cooperating transceiver disposed external to the body. A power circuit 160 which may include components used to receive and convert power from a source external to the body, and optionally, a battery, is shown coupled to the electronics module, and in turn, to the electronic component 100. In one example, the power circuit can comprise a transcutaneous energy transfer system ("TET") (not shown) by which power is transferred across the skin from an external coil to an implanted internal coil coupled thereto electromagnetically such that no driveline is required to pierce the skin.

With further reference to FIG. 7, the electronic component 100 may include a thin flexible support structure 112 typically composed of dielectric material, on which one or more electronic devices 110 and electrically conductive traces 114 are supported. In one example, the flexible support structure can include a dielectric material such as a flexible polyimide material of thickness typically greater than 50 micrometers ("microns"), the support structure being substantially inextensible in directions orthogonal to a direction of the support structure's thickness. In one example, the flexible support structure is made of polyimide material such as sold under the trade mark Kapton® from DuPont™.

In one example, the electronic devices and traces can be fabricated, e.g., printed or patterned, on a support structure 112 having flexible construction. Then, the support structure 112 can be adhered to an outwardly-facing surface 153 of the inner housing.

In another example, the electronic device and traces can be fabricated on a flexible support structure 112 supported as a decal temporarily on an underlying structure. Then the decal can be transferred from the underlying structure to the surface 153 of the inner housing.

In yet another example, the electronic devices and traces can be fabricated on a transfer structure and then transferred to the surface of the flexible support structure. Then, the flexible support structure can be adhered to the surface 153 of the inner housing. In one embodiment, an encapsulation 120 can be provided as shown covering the one or more devices 110 and traces 114.

In a particular embodiment, the support structure 112 may be made of or comprise flexible dielectric materials having specific properties making it capable of being stretched as utilized in a configuration when a tensile force is applied to the support structure in directions 132, 134 parallel to a surface of the support structure 112. In such case, the one or more electronic devices 110 may be configured to output a signal in relation to a degree to which such devices are stretched.

Figure 8:
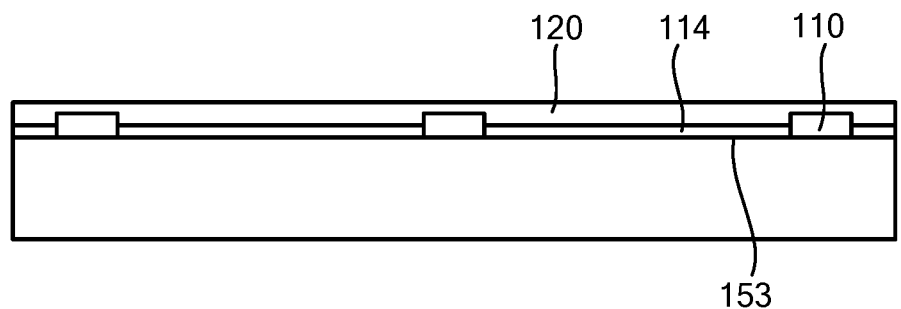
FIG. 8 depicts an electronic component in accordance with a variation of the embodiment of the invention seen in FIG. 7.

In variation, as seen in FIG. 8, the one or more electronic devices and traces can be printed or patterned directly on a surface 153 of the housing which surrounds the rotor 14. Otherwise, the one or more electronic devices and traces can be fabricated on other structure and then transferred to the surface 153 of the housing after fabrication. In either case, the electronic devices and traces can directly contact the surface 153, and the flexible support structure 112 can be omitted. A third example differs from the structure shown in either FIG. 7 or FIG. 8 in that a layer of dielectric material (not shown) can be attached to the surface 153, and then the one or more electronic devices and traces can be fabricated on the layer of material after such layer has been attached to the surface 153.

In a particular embodiment, the electronic component may include one or more transducers which are configured to sense a change in a magnetic field based on movement of a blood flow-driving actuator of the pump. For example, in an implementation as seen in FIGS. 1-5, the actuator is an impeller of the pump which is integral with a rotor driven by the pump's electromagnetic stator. The rotor 14 has a plurality of magnetic poles 56 thereon which are caused to rotate during operation of the pump under influence of a magnetic field produced by the stator. The one or more electronic devices 110 of the component 100 in such case may implement one or more transducers configured to sense a change in a magnetic field. Referring to FIG. 3, in a particular embodiment, the one or more transducers 116 can include one or more Hall effect sensors which are configured to detect a change in a magnetic field caused by movement of the magnetic poles of the rotor. For example, to detect a rotational velocity of a rotor having magnetic poles which are spaced apart from one another in a circumferential direction of the rotor, a signal from a Hall effect sensor can be used. In such case, a Hall effect sensor can produce signals representative of a frequency at which each magnetic pole of the rotor passes closest to the Hall effect sensors, such signals being closely correlated with a rotational speed of the rotor.

In one embodiment, the one or more transducers can output a signal representative of a rotational speed of a rotor of the blood pump. With further reference to FIG. 6, in some cases, the electronics module 140 may include a signal processor which is configured to process the signal from the one or more transducers to thereby generate an estimate of the rate of blood flow as discussed above. The electronics module 140 may further include a transmitter which is configured to transmit a second signal based on the estimated rate of blood flow, the second signal transmitted over the air or through a percutaneous drive line to circuitry external to the body.

In other variations, the system can be used to monitor operation of a pulsatile blood pump (not shown). A pulsatile blood pump differs from the blood pump seen in FIGS. 1-5 in that the actuator of the pulsatile blood pump can be a piston which reciprocates within a lumen of the pump. In this case, the one or more transducers arranged on a surface of a housing of the pulsatile pump are configured to detect a rate of reciprocation of the piston. From this information and information about the piston's stroke and the bore in which it moves, a blood flow rate of the pulsatile pump can be estimated.

In another example, the transducers implemented by the electronic devices 110 may comprise an emitter of optical wavelength energy and a detector of optical wavelength energy, wherein the emitter and the detector are arranged across a lumen of the blood pump in which the actuator drives the blood flow, such that emitted infrared energy passes through the inner housing into the lumen and passes through the blood before striking the detector at a second location. In this case, the inner housing will be translucent or transparent to optical wavelength energy at wavelengths of interest. In particular embodiments, the inner housing can be made of or can comprise ceramic material, glass or polymeric material which is translucent or transparent to the optical wavelength energy at wavelengths of interest. In one embodiment, the optical wavelength energy can be infrared energy. Referring to FIG. 3, for example, an infrared detector 118-2 can be disposed at a location across some portion of the lumen from an infrared emitter 118-1 such that the detector 118-2 can receive infrared energy passing through the blood and passing by the actuator. From signal characteristics of the detected infrared energy, parameters related to the pump's operation can be determined. With transducers that generate and detect optical wavelength energy, the inner housing is translucent thereto so that the optical wavelength energy at wavelengths of interest can travel from the optical emitter through the inner housing into the lumen and through the blood and are then received by the detector. In this way, the emitter and the detector can both be precluded from contact with blood within the space between the inner housing and the outer housing, such that neither the emitter nor the detector will require biocompatible construction, as neither will be in contact with the blood.

In a particular example, a position of the rotor within the pumping chamber or a displacement of the rotor within the pumping chamber can be determined directly by analyzing characteristics of the energy detected by one or a plurality of detectors of the emitted infrared energy. During operation of the blood pump, the displacement of the rotor in one or more degrees of freedom which may include displacement in a side to side direction (x, y), axial (z), and/or angular directions (e.g., tilt) can vary. Measurement of rotor-dynamic displacement can provide valuable information regarding function of the pump under normal as well as different operating conditions and loads.

In another example, the rotational speed of the rotor can be determined, from which and together with other pump parameters, an estimate of the blood flow rate can be determined.

In a particular example, the plurality of transducers implemented by the electronic devices can be configured to generate a second signal from infrared energy received after passing through blood within the pump. In one embodiment, the second signal can be representative of a level of oxygen saturation within the blood.

In another example, infrared transducers which implement a generator of infrared signal energy and a detector of infrared signal energy may be used exclusively for detecting a level of oxygen saturation within the blood. In one embodiment, such transducers can be the only transducers of electronic component 100.

In yet another example, the plurality of transducers may comprise a generator and a detector of sonic or ultrasonic energy. As in the above example containing an infrared emitter and infrared detector pair 118-1, 118-2, the generator and detector can be disposed at locations which span a distance of the lumen 60 of the blood pump through which blood flows while the pump is operating. The detector can be disposed at a location downstream from the generator and can be configured to receive ultrasonic energy from the generator after passing through the blood. In one example, signal characteristics of the detected signal can be analyzed to determine a rate of blood flow through the pump. In one example, the detected ultrasound signal at the downstream location can undergo a frequency shift relative to the applied ultrasound signal at the upstream location, which frequency shift is correlated with the velocity of blood flowing through the inner housing. In this way, the rate of blood flow can be determined.

In one embodiment, the one or more transducers may comprise an accelerometer. The accelerometer may be configured to generate a signal representative of vibration associated with the operating state of the blood pump.

Figure 9:
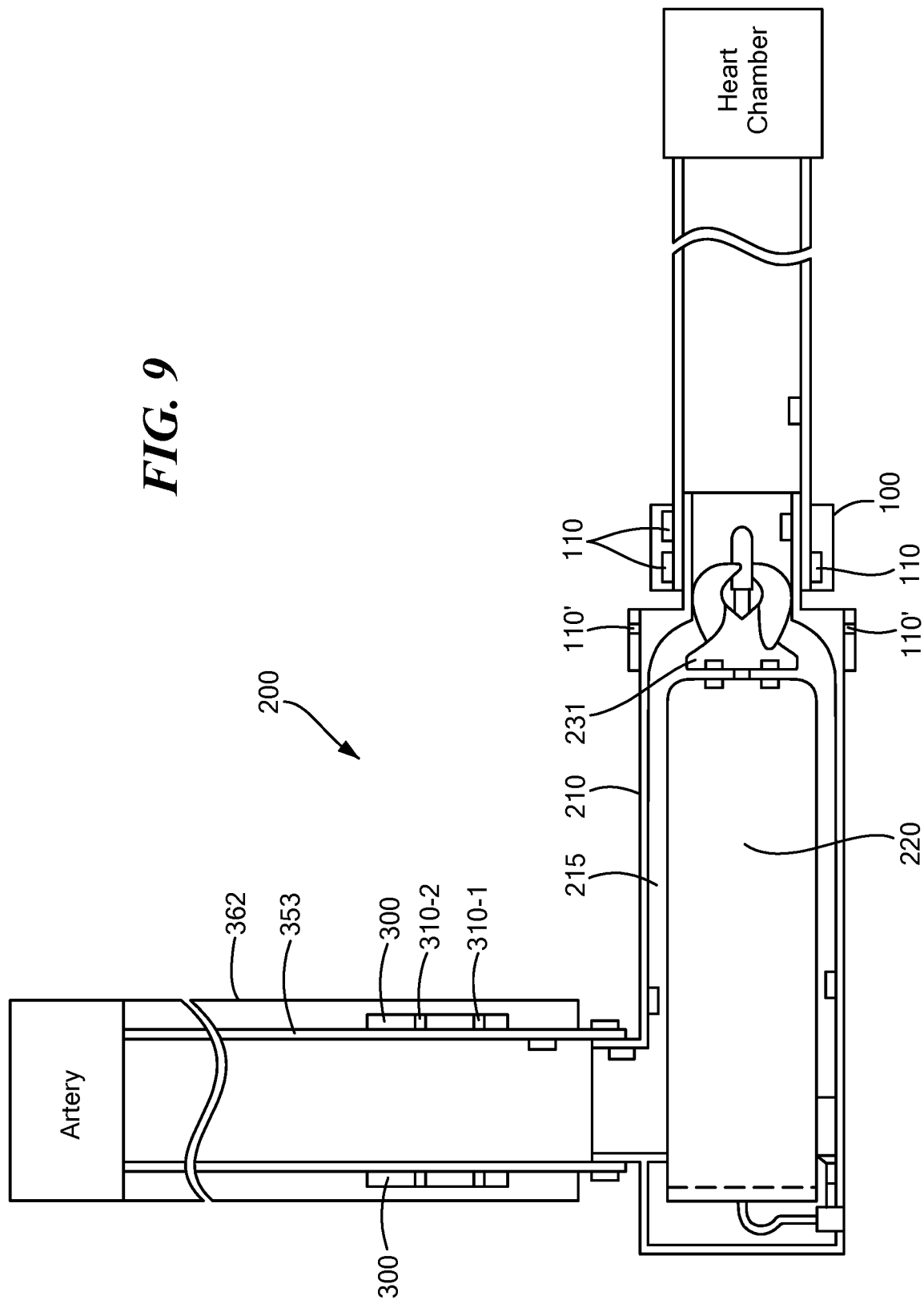
FIG. 9 is an elevational view illustrating an alternative implementation in which an impeller of the blood pump is driven by a motor magnetically coupled to the impeller.
Figure 10:
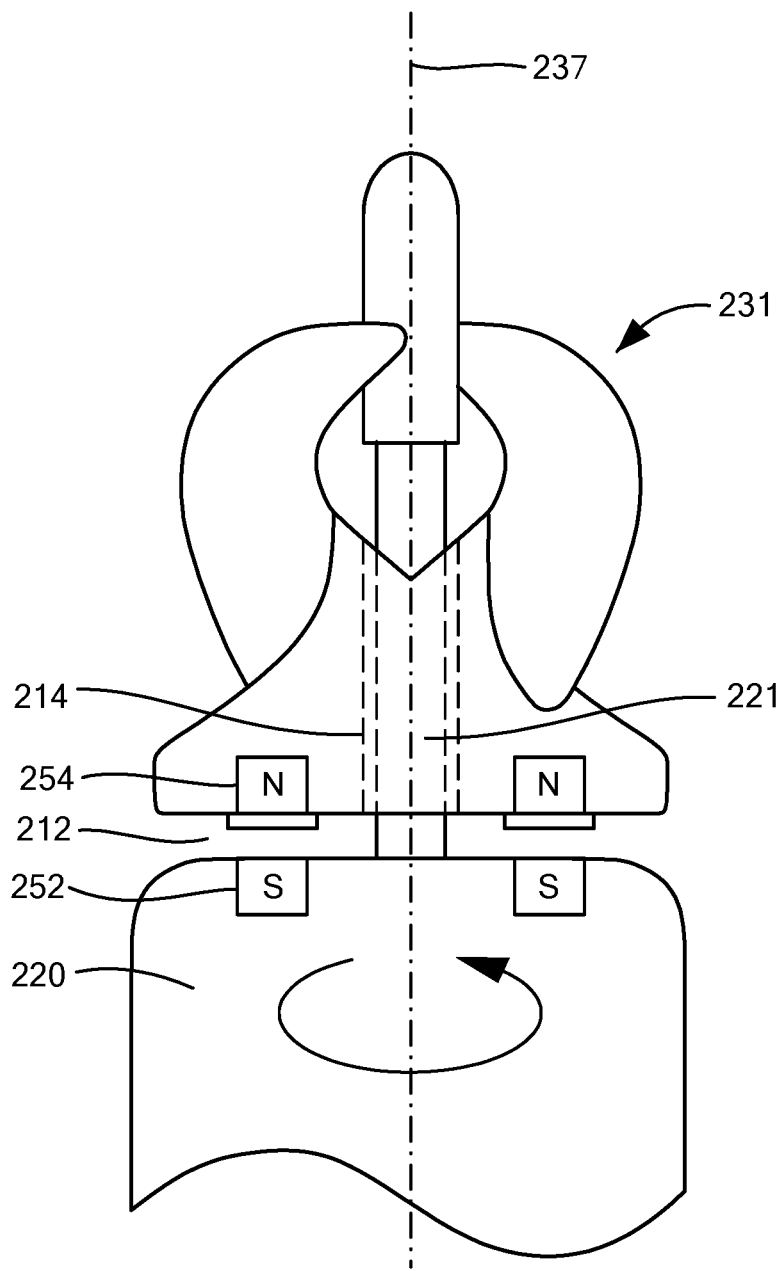
FIG. 10 is another elevational view illustrating an alternative implementation in which an impeller of the blood pump is driven by a motor magnetically coupled to the impeller.

In another example as seen in FIGS. 9-10, a blood pump system 200 includes a housing 210 surrounding a rotational drive assembly including motor 220 and fluid drive element such as impeller 231. In some embodiments, system 200 comprises a rotational drive assembly similar to that described in U.S. Publication No. 2016/0193396, which is a publication of U.S. application Ser. No. 14/590,485 entitled "Axial Flow Rotor With Downstream Bearing Wash Flow," the disclosure of which is incorporated by reference herein and annexed hereto as Exhibit D; or alternatively, U.S. Pat. No. 6,116,862 entitled "Blood Pump"; or U.S. Pat. No. 6,176,848 entitled "Intravascular Blood Pump", the disclosures of which are incorporated by reference herein. Impeller 231 is magnetically coupled with and driven about a rotational axis by a spinning drive mechanism 220 having a set of magnetic poles 252 coupled across gap 212 with corresponding magnetic poles 254 of the impeller 231 through force of magnetic attraction. Drive mechanism 220 includes a motor which rotates poles 252 around the common axis 237 of the drive motor and impeller. A supporting element such as a shaft 221 may extend through a central opening 214 of the impeller and can support the impeller while the impeller is rotating and held in place axially by the magnetic attraction from the drive mechanism 220. The pump chamber 215 includes the open space between a tubular portion of the housing 210 and other components of the pump such as impeller 231, shaft 221 and motor 220.

In the blood pump system as shown in FIGS. 9-10, the fluid-driving actuator of the pump is an impeller 231 which is driven by but physically distinct from the motor which drives it. In one example, one or more electronic devices 110 or devices 110' of an electronic component 100 as described above can be provided or distributed over a surface of the housing of the pump at locations adjacent the impeller 231 or alternatively, at locations adjacent to rotating elements of the motor 220. For example, any or all transducers such as discussed above can be provided associated with a surface of an inner housing of the blood pump for monitoring an operation of the pump, determining a rate of blood flow, or other parameter. In a further example, blood flow measurement can be provided by ultrasonic transducers 310-1, 310-2 of electronic component 300 associated with a surface 353 of downstream structure, a cannula, or other component of a circulatory assist system, where component 300 has the features of electronic component 100 described above. In a particular example, an outer housing 362 can overlie the electronic component 300 and enclose the component 300 within a sealed space.

Figure 11:
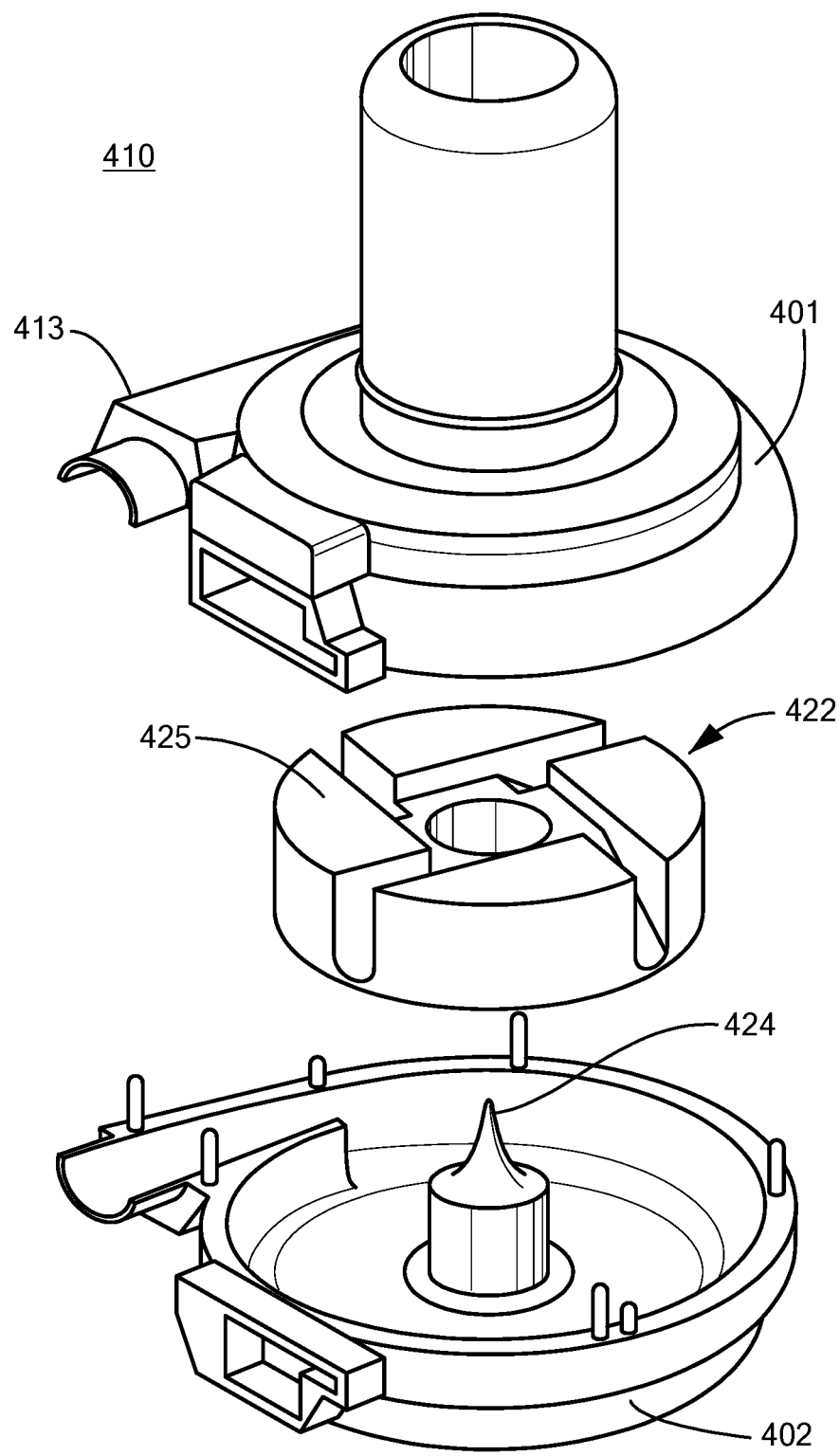
FIG. 11 is an exploded perspective view illustrating a blood pump in accordance with an embodiment of the invention.
Figure 12:
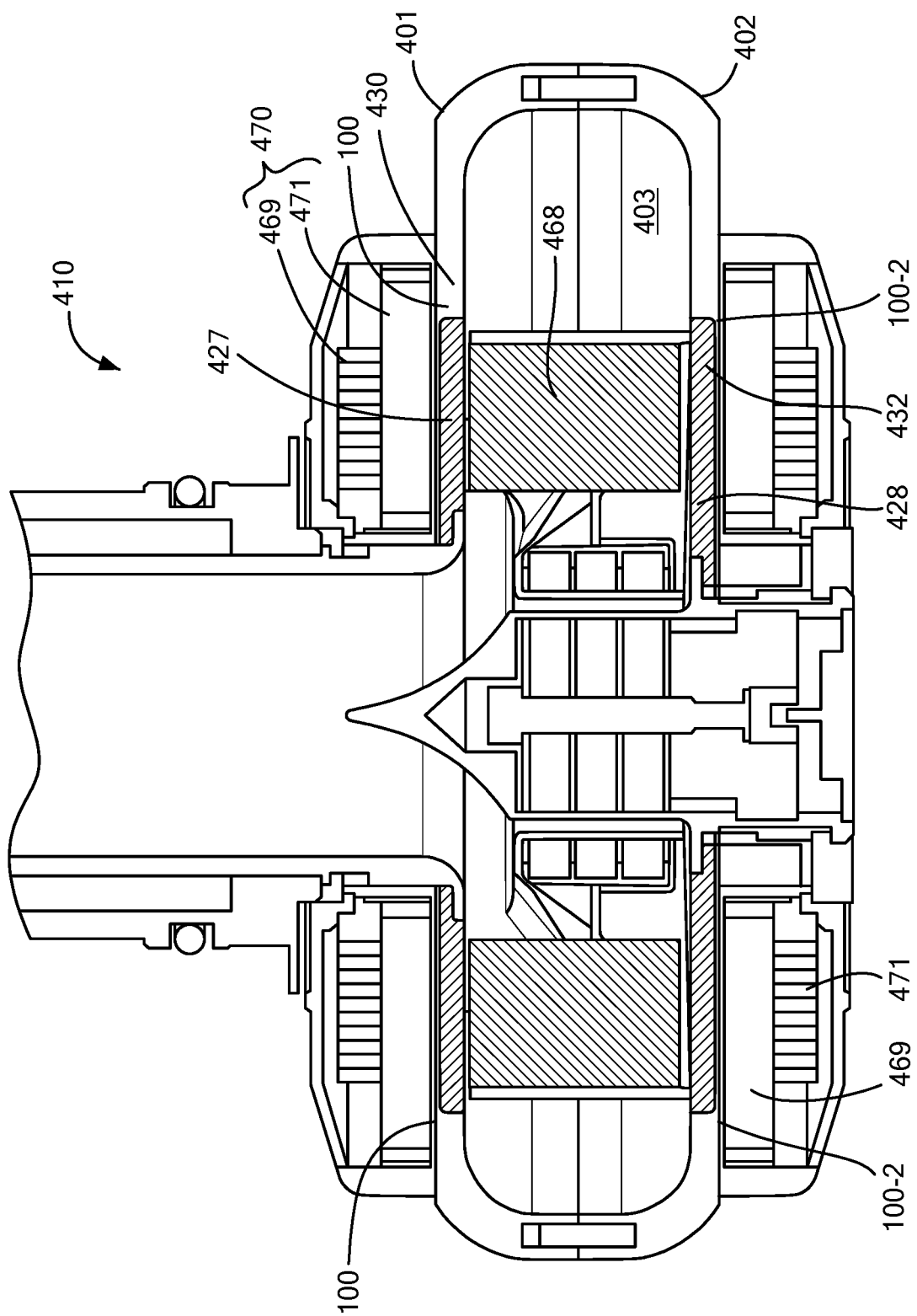
FIG. 12 is a sectional view further illustrating a blood pump in accordance with the embodiment of the invention seen in FIG. 11.

Referring now to FIGS. 11 and 12, in another embodiment, the electronic component as described above can be applied or integrated into a rotary blood pump 410 such as disclosed in commonly owned U.S. Pat. No. 7,997,854, the disclosure of which is incorporated herein by reference. As seen therein, the rotary pump has a casing comprising an upper casing 401 and a lower casing 402 which together define a generally cylindrical pumping chamber 403. A generally cylindrical motor rotor 422 within the pumping chamber functions as an impeller (hereinafter "impeller 422") to drive a flow of blood from a position adjacent a center post 424 at an inlet to the pumping chamber 403 to a position that is in radial direction beyond a periphery 425 of the impeller 422 where the blood then exits the pump through an outlet 413 in a direction substantially tangential to the cylindrical periphery of the impeller 422. The upper and lower casings 401, 402 of the pump 410 can be made of a biocompatible material such as alumina, titanium, ceramic, glass or polymer material. In the embodiment illustrated in FIGS. 11-12, disks 427, 428 of ceramic or other durable material can be positioned at an inner surface of the upper casing 401 and at an inner surface 402 of the lower casing, the disks functioning to minimize friction on startup of the pump and to provide very flat surfaces against which hydrodynamic thrust bearings at the impeller top surface can operate.

A ferromagnetic or iron bar 471 and windings 469 are further shown in FIG. 12, these components configured to generate a rotating magnetic field which, coupled with magnetic poles of the impeller, e.g., permanent magnets 468 or magnetized regions of the impeller, causes the impeller 422 to rotate and drive a flow of blood through the pump 410. The windings 469 and iron bar 471 operate as an electromagnetic stator 470 of the rotary blood pump.

FIG. 12 illustrates an electronic component 100 which can be disposed between a surface of an inner housing of the rotary blood pump and the electromagnetic stator 470. In one embodiment, the electronic component 100 can be adhered to or printed on an outwardly facing surface 430 of the inner housing defined by the upper casing 401, and one or more of the electronic devices thereon can be disposed between that surface 430 and the electromagnetic stator. Another electronic component 100-2 having a structure and function such as electronic component described above can be adhered to or printed on an outwardly facing surface 432 of the inner housing defined by the lower casing 402, and one or more of the electronic devices thereon can be disposed between that surface 432 and the electromagnetic stator. In one embodiment, the electronic component 100 can be adhered to or printed on an outwardly-facing surface of a disk 427 provided in the upper casing 401. Similarly, another such electronic component 100-2 can be adhered to or printed on an outwardly-facing surface of a disk 427 provided in the upper casing 401.

As in the above-described examples, the electronic components 100, 100-2 can be disposed in locations which are encased within the outer housing of the rotary pump 410 defined by the upper and lower casings 401, 402, and therefore are not in contact with the blood. Accordingly, in such case, the electronic components need not be made of biocompatible materials.

In one embodiment, variations in the magnetic field can be detected which are due to passing of magnets or magnetized portions of the impeller past locations at which transducers, e.g., Hall effect sensors, of the electronic component are disposed, which detected variations can then be used to determine a rotational speed of the impeller and provide other information, for example, position or displacement of a rotor in one or more degrees of freedom of the rotor. In the particular case of the rotary pump, since the flow of blood towards the outlet 413 is in a circumferential direction within an annular portion of the pumping chamber 403 in a radial direction beyond the periphery 425 of the impeller 422, transducers can be arranged at different circumferential positions within that annular portion to collect data at the different circumferential positions which are upstream and downstream relative to the flow of blood within the annular portion.

Thus, in one embodiment, an optical emitter and an optical detector of the electronic component 100 can be arranged at the different circumferential positions for use in collecting data regarding the operation of the pump, rotational speed, level of oxygen saturation, and flow characteristics. In another embodiment, the electronic component may include electronic devices which implement a generator and a detector of sonic or ultrasonic energy and which can be utilized such as in the example discussed above relative to FIGS. 3 and 4.

It will be appreciated that the various dependent features set forth in the application therein can be combined in different ways than presented in the paragraphs below. It will also be appreciated that the features described in connection with individual embodiments can be shared with others of the described embodiments.

Although the invention herein has been described with reference to particular embodiments, it is to be understood that these embodiments are merely illustrative of the principles and applications of the various embodiments described herein. It is therefore to be understood that numerous modifications can be made to the illustrative embodiments and that other arrangements can be devised without departing from the spirit and scope of the above-described embodiments of the invention. Certain features of the disclosure are further described in the paragraphs below.

What is claimed is:

1. An implantable blood pump, comprising:
a housing sized to be implanted within a body of a patient;
a rotor surrounded by the housing and configured to drive a flow of blood within the body;
an electronic component engaged with a surface of the housing, the electronic component including one or more thin film active electronic devices, the one or more electronic devices having one or more transducers configured to generate a signal based on movement associated with operation of the blood pump, the one or more transducers including at least one transducer configured to sense a change in a magnetic field caused by movement of the rotor and transducers configured to determine a level of oxygen saturation within the blood; and
a stator partially surrounding the housing, the stator magnetically coupled with the rotor and overlying at least one of the one or more transducers.

2. The blood pump of claim 1, wherein the one or more transducers comprise at least first and second transducers spaced apart from one another in at least a first direction parallel to a downstream direction of the blood flow.

3. The blood pump of claim 2, wherein the first transducer is configured to emit sonic energy and the second transducer is configured to receive sonic energy, respectively, wherein the sonic energy received by the second transducer is processable relative to the sonic energy emitted by the first transducer to determine a rate of blood flow through the pump.

4. The blood pump of claim 2, wherein the one or more transducers comprise a first transducer configured to emit infrared energy and a second transducer configured to receive infrared energy, respectively, wherein the infrared energy received by the second transducer is processable relative to the infrared energy emitted by the first transducer to determine an operating speed of the pump.

5. The blood pump of claim 1, wherein the one or more electronic devices are fabricated on an electrically insulating region at the surface of the housing.

6. The blood pump of claim 1, wherein the one or more transducers comprise an emitter of infrared energy and a detector of infrared energy, wherein the emitter and the detector of infrared energy are arranged across a lumen of the blood pump configured to carry blood in an operating state of the blood pump, and the detector is configured to receive infrared energy which passes through the blood in the lumen.

7. The blood pump of claim 1, wherein the one or more transducers includes a first plurality of transducers, wherein the electronic component further comprises a second plurality of transducers including a generator of infrared energy and a detector of infrared energy, wherein the detector is configured to receive infrared energy from the generator which passes through blood within the pump.

8. The blood pump of claim 1, wherein the one or more transducers includes a generator of ultrasonic energy and a detector of ultrasonic energy, wherein the generator and the detector are arranged across a lumen of the blood pump through which blood flows in an operating state of the blood pump, and the detector is configured to receive ultrasonic energy which passes through the blood from the generator.

9. The blood pump of claim 1, wherein the one or more transducers include at least one accelerometer, and the at least one accelerometer is configured to monitor vibration associated with operation of the blood pump.

10. The blood pump of claim 1, wherein the one or more transducers are configured to directly receive electromagnetic waves or mechanical energy within the body representative of a monitored bodily function and are configured to generate an electrical signal representative of the monitored bodily function.

* * * * *